United States Patent [19]

Mossé et al.

[11] Patent Number: 4,916,156
[45] Date of Patent: Apr. 10, 1990

[54] AROMATIC DERIVATIVES, THEIR PREPARATION AND THEIR USE AS ANTIMICROBIAL AGENTS

[75] Inventors: Madeleine Mossé, Montpellier; Vincenzo Proietto, Saint-Georges D'Orques, both of France

[73] Assignee: Sanofi, Paris, France

[21] Appl. No.: 178,327

[22] Filed: Apr. 6, 1988

[30] Foreign Application Priority Data

Apr. 10, 1987 [FR] France ................. 87 05165

[51] Int. Cl.$^4$ ................. A01N 47/06; A01N 37/10; C07C 154/00; C07C 87/32
[52] U.S. Cl. ................. 514/510; 514/512; 514/530; 514/531; 514/534; 514/535; 514/546; 514/550; 514/552; 558/248; 558/270; 558/271; 558/272; 558/275; 560/20; 560/22; 560/100; 560/102; 560/104; 560/106; 560/107; 560/121; 560/122; 560/123; 560/124; 560/125; 560/126; 560/152; 560/187; 560/250
[58] Field of Search ................. 560/20, 22, 106, 107, 560/100, 102, 104, 121, 122, 123, 124, 125, 126, 152, 187, 250; 514/510, 534, 535, 530, 531, 546, 550, 552, 512; 558/248, 270, 271, 272, 275

[56] References Cited

U.S. PATENT DOCUMENTS

| | | | |
|---|---|---|---|
| 2,680,765 | 6/1954 | Sprague | 560/106 |
| 2,971,018 | 2/1961 | Shapiro | 560/106 |
| 3,073,741 | 1/1963 | Vecchi | 514/534 |
| 3,767,810 | 10/1973 | Abdallah | 560/104 |
| 4,075,241 | 2/1978 | Bellasio et al. | 560/73 |

FOREIGN PATENT DOCUMENTS

| | | |
|---|---|---|
| 1445968 | 11/1969 | Fed. Rep. of Germany . |
| 3525 M | 7/1964 | France . |
| 3660 M | 7/1964 | France . |
| 2137722 | 12/1972 | France . |
| 863223 | 3/1961 | United Kingdom . |
| 1434826 | 5/1976 | United Kingdom . |

OTHER PUBLICATIONS

Dimmock et al., *J. Pharm. Sci.*, vol. 67, No. 3, Mar. 1978.
Streitwieser, Jr., and Heathcock, *Introduction to Organic Chemistry* (1985) pp. 465 and 493.

*Primary Examiner*—Joseph Paul Brust
*Assistant Examiner*—MarySue Howard
*Attorney, Agent, or Firm*—Foley & Lardner Schwartz, Jeffery, Schwaab, Mack, Blumenthal & Evans

[57] ABSTRACT

The present invention relates to aromatic derivatives of the formula:

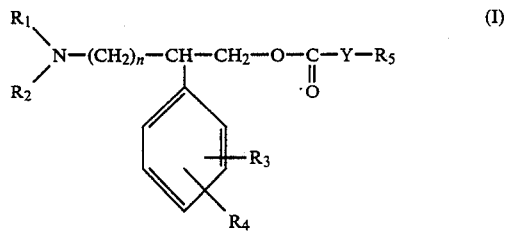

in which:
n represents an integer between 2 and 10;
$R_1$ and $R_2$ are identical or different and represent a cycloalkyl containing 3 to 6 carbon atoms or an alkyl containing from 1 to 6 carbon atoms which is unsubstituted or substituted by a phenyl or benzyl group; or
$R_1$ and $R_2$, together with the nitrogen atom to which they are bonded, form a heterocycle selected from pyrrolidin-1-yl, piperidino, azepin-1-yl, hexamethyleneimino, 4-methylpiperidino, 4-benzylpiperidino, 4-phenylpiperidino, 1,2,3,4-tetrahydroisoquinol-2-yl, morpholino and imidazol-1-yl groups;
$R_3$ represents a hydrogen, a halogen, a methyl or a phenyl;
$R_4$ represents a hydrogen, a halogen or a methyl; or $R_3$ and $R_4$, taken together with the benzene ring to which they are bonded, form a naphth-1-yl or naphth-2-yl group;
Y represents a direct bond, a methyleneoxy group, a methylenethio group or a vinylene group; and
$R_5$ represents an alkyl containing from 5 to 18 carbon atoms, a cycloalkyl containing from 3 to 8 carbon atoms, an adamantyl, naphth-1-yl or naphth-2-yl group, an unsubstituted phenyl group or a phenyl group substituted by one or 2 substituents selected from halogen atoms, the trifluoromethyl group, the nitro group and the phenyl group;
and to their salts with mineral or organic acids.

12 Claims, No Drawings

AROMATIC DERIVATIVES, THEIR PREPARATION AND THEIR USE AS ANTIMICROBIAL AGENTS

The present invention relates to novel aromatic derivatives substituted by an esterified (omega-amino)alkanol group.

The present invention also relates to the use of the compounds according to the invention in antiseptic or antimicrobial compositions such as disinfectants or preservatives, especially in the fields of pharmacy, cosmetology or agri-foodstuffs.

According to another feature, the present invention relates to the process for the preparation of the compounds according to the invention.

More precisely, the present invention relates to novel aromatic derivatives of the formula:

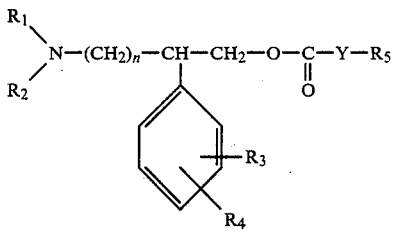

in which:

n represents an integer between 2 and 10;

$R_1$ and $R_2$ are identical or different and represent a cycloalkyl group containing 3 to 6 carbon atoms or an alkyl containing from 1 to 6 carbon atoms which is unsubstituted or substituted by a phenyl or benzyl group; or $R_1$ and $R_2$, together with the nitrogen atom to which they are bonded, form a heterocycle selected from pyrrolidin-1-yl, piperidino, azepin-1-yl, hexamethyleneimino, 4-methylpiperidino, 4-benzylpiperidino, 4-phenylpiperidino, 1,2,3,4-tetrahydroisoquinol-2-yl, morpholino and imidazol-1-yl groups;

$R_3$ represents a hydrogen, a halogen, a methyl or a phenyl;

$R_4$ represents a hydrogen, a halogen or a methyl; or $R_3$ and $R_4$, taken together with the benzene ring to which they are bonded, form a naphth-1-yl or naphth-2-yl group;

Y represents a direct bond, a methyleneoxy group, a methylenethio group or a vinylene group; and $R_5$ represents an alkyl containing from 5 to 18 carbon atoms, a cycloalkyl containing from 3 to 8 carbon atoms, an adamantyl, naphth-1-yl or naphth-2-yl group, an unsubstituted phenyl group or a phenyl group substituted by one or 2 substituents selected from halogen atoms, the trifluoromethyl group, the nitro group and the phenyl group;

and to their salts with mineral or organic acids.

More precisely, the present invention relates to compounds of formula (I) in which $R_3$ represents a hydrogen, a halogen, a methyl or a phenyl and $R_4$ represents a hydrogen, a halogen or a methyl.

The present invention also relates to compounds of formula (I) in which $R_3$ and $R_4$, taken together with the benzene ring to which they are bonded, form a naphth-1-yl or naphth-2-yl group.

5-Dimethylamino-2-(naphth-1-yl)pentyl 2,4-dichlorobenzoate and its salts are preferred compounds according to the invention.

In the present description, halogen denotes chlorine, bromine, iodine or fluorine.

The process according to the invention comprises esterifying the amino alcohol of the formula:

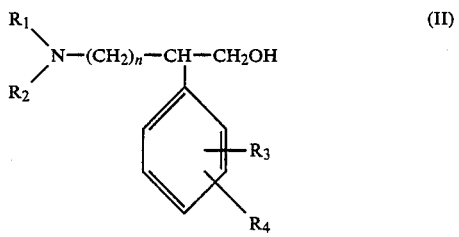

in which $R_1$, $R_2$, $R_3$, $R_4$ and n are as defined above, or one of its salts with a mineral or organic acid, with an acid or an acid halide of the formula:

in which Y and $R_5$ are as defined above and Z represents a halogen atom or the OH group.

The reaction is carried out at a temperature which can vary between 50° C. and 120° C., either using the acid or the acid halide as the solvent, or in an unreactive solvent such as dichloroethane or pyridine.

If the reaction is carried out on a salt of the amino alcohol (II), the compound (I) according to the invention is also prepared in the form of a salt.

The amino alcohol (II) is prepared by reducing the ester or the corresponding acid of the formula:

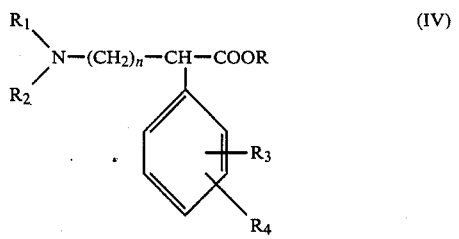

in which $R_1$, $R_2$, $R_3$ and $R_4$ are as defined above and R represents hydrogen or an alkyl group.

This reduction is effected by known means such as reaction with a reducing agent or an electrolysis reaction in an acid medium. The reducing agent used is a metal hydride, if appropriate in the presence of a catalyst. More particularly, the reduction of the acid or the ester (IV) to give the amino alcohol (II) can be effected with boron hydride, aluminum hydride, lithium borohydride, aluminum borohydride, sodium borohydride, sodium aluminum hydride, lithium aluminum hydride or another boron hydride such as borane dimethylsulfide or benzo-1,2,3-dioxaborole. The reduction is preferably carried out on the acid (R=H) or on the ethyl ester (R=$C_2H_5$) by reaction with Vitride® (sodium bis(2-methoxyethoxy)aluminum hydride) in an inert solvent such as benzene or toluene, at a temperature between room temperature and 80° C. The compound obtained is isolated by the customary methods, for example by simple precipitation.

The acids and their esters (IV) are prepared by known methods. The starting material used is phenylacetonitrile substituted on the benzene ring by $R_3$ and $R_4$, or naphth-1-ylacetonitrile or naphth-2-ylacetonitrile, depending on the target compound, this is reacted with sodium amide in an inert solvent heated to the reflux temperature, a chloroalkylamine of the formula:

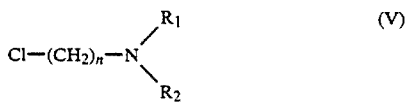

is added and the mixture is heated to the reflux temperature of the solvent to form the compound:

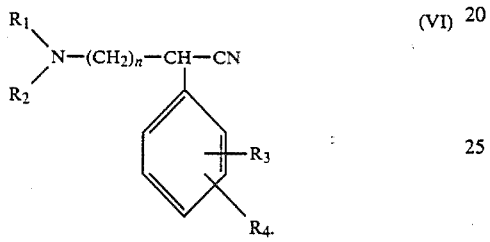

The nitrile (VI) is hydrolyzed in a strong acid medium (pH below 2) to give the corresponding acid, which is esterified, if appropriate, with an alkyl group R by known methods.

The acid halides or the corresponding acids (III) are known.

The examples which follow illustrate the invention without however implying a limitation.

EXAMPLE 1

4-Dimethylamino-2-(naphth-1-yl)butyl 2,4-dichlorobenzoate hydrochloride: SR 44083 A (A) 4-Dimethylamino-2-(naphth-1-yl)butanol hydrochloride (a) 4-Dimethylamino-2-(naphth-1-yl)butyronitrile 6.9 g of sodium amide are added in small portions to 29.4 g of naphth-1-ylacetonitrile in 250 ml of anhydrous benzene and the mixture is heated at 80° C. for 2 hours. It is cooled to +40° C., 19 g of 2-chlorodimethylaminoethane are added dropwise and the mixture is then heated again at 80° C. for 4 hours. It is cooled and 200 ml of water are added. After decantation, the organic phase is extracted with a 10% solution of hydrochloric acid. The aqueous phase is washed with ether, neutralized with a 10% solution of sodium hydroxide and extracted with ether and the extract is then washed with water and dried over sodium sulfate. 24 g of the expected product are obtained after evaporation of the solvent.

(b) 4-Dimethylamino-2-(naphth-1-yl)butyric acid 19 g of the product obtained in the previous step are refluxed for 2 hours in 150 ml of a solution of acetic acid/sulfuric acid/water (1/1/1 by volume). The mixture is cooled, diluted with water and washed twice with ether. The aqueous phase is neutralized with a 30% solution of sodium hydroxide and washed with ether and the aqueous phase is then acidified again with concentrated hydrochloric acid and evaporated to dryness. The residue is extracted with ethanol. After evaporation of the ethanol, the residue is recrystallized from an ethanol/ethyl ether mixture to give 9 g of the expected product.

Melting point: 130°-135° C. with decomposition.

(c) 4-Dimethylamino-2-(naphth-1-yl)butanol hydrochloride 5.1 g of the product obtained above are added in small portions to 11.8 g of Vitride ® [sodium bis(2-methoxyethoxy)aluminum hydride] at a concentration of 70% in toluene. The mixture is heated at 80°-90° C. for 3 hours and then cooled to +10° C. and poured into water.

The mixture is extracted with ether and the ether extract is washed with water and dried over sodium sulfate. The residue is taken up with dry ethyl ether, a solution of hydrogen chloride in ether is added and the mixture is evaporated to dryness in vacuo. The residue is then taken up with dry isopropyl alcohol and solubilized by refluxing. The solution is cooled and anhydrous ethyl ether is then added dropwise. The precipitate formed is filtered off, then washed several times with anhydrous ether and dried and then recrystallized from an ethanol/isopropyl ether mixture to give 3.3 g of the expected product.

Yield: 60%.

Melting point: 163° C.

1.1. SR 44083 A 2.9 g of the alcohol prepared in the previous step and 10 ml of 2,4-dichlorobenzoyl chloride are heated at 100° C. for half an hour. The mixture is cooled and precipitated in ether and the precipitate is filtered off, washed with ether, dried in vacuo and recrystallized from an isopropyl alcohol/ethyl ether mixture to give 4 g of the expected product.

Yield: 87%.

Melting point: 147°-150° C.

EXAMPLE 2

2-(3,4-Dichlorophenyl)-4-hexamethyleneiminobutyl 2,4-dichlorobenzoate hydrochloride: SR 44102 A 1.2.

2-(3,4-Dichlorophenyl)-4-hexamethyleneiminobutanol hydrochloride 1.2. (a)1 2-(3,4-Dichlorophenyl)-4-hexamethyleneiminobutyronitrile 4 g of sodium amide are added in small portions to 16.5 g of 3,4-dichlorophenylacetonitrile in 200 ml of anhydrous ether and the mixture is refluxed for 2 hours. 16.10 g of N-hexamethyleneimino-2-chloroethane are then added dropwise, the mixture is refluxed for 5 hours and cooled, 200 ml of water are added and the organic phase is decanted and extracted with 300 ml of 10% hydrochloric acid. The aqueous phase is washed with ether, neutralized with 30% sodium hydroxide and extracted with ether. The organic phase is washed with a saturated aqueous solution of sodium chloride and dried over magnesium sulfate and the solvent is then evaporated off to give 26 g of the expected product.

Yield: 84%.

1.2. (b) 2 Methyl 2-(3,4-dichlorophenyl)-4-hexamethyleneiminobutanoate 20 g of the product obtained in the previous step are refluxed for 2 hours in 90 ml of a solution of water/sulfuric acid/acetic acid (1/1/1 by volume). The mixture is cooled, poured into 200 ml of water and washed with ether. The aqueous phase is brought to pH 10 by the addition of 30% sodium hydroxide, washed with ether and acidified to pH 1 with hydrochloric acid. The water is evaporated off and the residues are taken up with hot methanol. Half the methanol is evaporated off, a few drops of sulfuric acid are added and the mixture is refluxed for 5 hours. The solvent is removed, the remaining oil is taken up with water and the mixture is neutralized with 30% sodium hydroxide. It is extracted with ether and the extract is washed with a saturated aqueous solution of sodium chloride, dried over magnesium sulfate and then evaporated to dryness to give 15.1 g of the expected product.

Yield: 76.5%.

1.2. (c) 3 2-(3,4-Dichlorophenyl)-4-hexamethyleneiminobutanol 12.6 g of Vitride ® (sodium bis(2-methoxyethoxy)aluminum hydride) at a concentration of 70% in toluene are added dropwise at 0° C. to 14.5 g of the product obtained in the previous step. The reaction is allowed to proceed for 30 minutes at room temperature. The reaction mixture is poured into water and extracted with ether, the extract is washed with a saturated aqueous solution of sodium chloride and dried over magnesium sulfate and the solvent is then evaporated off. The residue is taken up in a solution of hydrogen chloride in ether. After evaporation of the solvent, the product is taken up in 20 ml of isopropyl alcohol and anhydrous ether is then poured in dropwise until the product crystallizes. The precipitate is washed with ether and dried in vacuo to give 12 g of product.

Yield: 81%.
Melting point: 155° C.

1.2. SR 44102 A 1.5 g of the alcohol obtained in the previous step are heated at 100° C. for 30 minutes in 10 ml of 2,4-dichlorobenzoyl chloride. The mixture is then precipitated in ether and the precipitate is filtered off, washed with ether, dried in vacuo and recrystallized from an ether/isopropyl alcohol mixture to give 1.9 g of the expected product.

Yield: 90%.
Melting point: 179°–181° C.

EXAMPLE 3

2-(3,4-Dichlorophenyl)-5-dimethylaminopentyl p-chlorocinnamate hydrochloride: SR 44429 A (A) 2-(3,4-Dichlorophenyl)-5-dimethylaminopentanol hydrochloride (a) 2-(3,4-Dichlorophenyl)-5-dimethylaminovaleronitrile 3.9 g of sodium amide are added in small portions to a solution of 18.6 g of 3,4-dichlorophenylacetonitrile in 200 ml of anhydrous ether. The mixture is refluxed for 2 hours, 12.1 g of 3-chlorodimethylaminopropane are added and refluxing is continued for 2 and a half hours. The mixture is cooled, water is added and the organic phase is decanted. It is washed with water and extracted with 10% hydrochloric acid. The aqueous phase is then neutralized with 30% sodium hydroxide and extracted with ether and the solvent is evaporated off to give 17 g of the expected product.

Yield: 62.5%.

(b) Methyl 2-(3,4-dichlorophenyl)-5-dimethylaminopentanoate 17 g of the product obtained above are refluxed for 5 hours with 75 ml of a solution of sulfuric acid/acetic acid/water (1/1/1 by volume). The mixture is cooled, poured into water and washed with ether. The aqueous phase is neutralized with 30% sodium hydroxide and the oil which decants is separated off. It is washed with ether and then acidified with 35% hydrochloric acid. It is then taken up with methanol and a few drops of sulfuric acid and refluxed overnight. After cooling, the methanol is evaporated off and the residue is neutralized with sodium bicarbonate and extracted with ether to give 8 g of product.

(c) 2-(3,4-Dichlorophenyl)-5-dimethylaminopentanol hydrochloride 8 g of the ester obtained in the previous step are reduced at room temperature with 6.8 g of Vitride ® at a concentration of 70% in toluene. The mixture is poured into iced water and extracted with ether and the extract is washed with water, dried over magnesium sulfate and evaporated to dryness. The residue is taken up with ether and a solution of hydrogen chloride in ether is then added. The precipitate is filtered off, dried and recrystallized from ether to give 8 g of the expected product.

Yield: 98%.
Melting point: 115°–117° C.

(B) SR 44429 A 3.1 g of the product obtained in the previous step and 4.02 g of p-chlorocinnamoyl chloride are refluxed for 3 hours in 50 ml of dichloroethane. The mixture is cooled and evaporated to dryness and the residue is taken up with the minimum amount of dichloroethane and precipitated in ether to give 3 g of the expected product, which is recrystallized from an ethanol/ether mixture.

Yield: 64%.
Melting point: 136°–137° C.

EXAMPLE 4

4-(4-Benzylpiperidino)-2-(naphth-1-yl)butyl 2,4-dichlorophenoxyacetate hydrochloride: SR 44541 A (A) 4-(4-Benzylpiperidino)-2-(naphth-1-yl)butanol hydrochloride (a) 4-(4-Benzylpiperidino)-2-(naphth-1-yl)butyronitrile 2 g of sodium amide are added in small portions to a solution of naphth-1-ylacetonitrile in 150 ml of anhydrous ether and the mixture is refluxed for 5 hours. 11.8 g of 2-(4-benzylpiperidino)chloroethane are then added and the mixture is refluxed again for 3.5 hours. 200 ml of water are added and the organic phase is decanted and extracted with 300 ml of 10% hydrochloric acid. The aqueous phase is washed with ether, neutralized with 30% sodium hydroxide and extracted with ether. The organic phase is washed with a saturated aqueous solution of sodium chloride and dried over magnesium sulfate and the solvent is then evaporated off to give 16.4 g of the expected product.

(b) Methyl 4-(4-benzylpiperidino)-2-(naphth-1-yl)butanoate 14 g of the product obtained in the previous step are refluxed for 2 hours in 75 ml of a solution of water/sulfuric acid/acetic acid (1/1/1 by volume).

The mixture is cooled, poured into 200 ml of water and washed with ether. The aqueous phase is brought to about pH 10 by the addition of 30% sodium hydroxide, washed with ether and acidified to pH 1 with hydrochloric acid, the water is then evaporated off and the residues are taken up with hot methanol. After evaporation of half the methanol, a few drops of sulfuric acid are added and the mixture is then refluxed for 5 hours. The solvent is removed and the remaining oil is taken up with water and neutralized with 30% sodium hydroxide. The mixture is extracted with ether and the extract is washed with a saturated aqueous solution of sodium chloride, dried over magnesium sulfate and evaporated to dryness to give 13.7 g of the expected product.

Yield: 87%.

(c) 4-(4-Benzylpiperidino)-2-(naphth-1-yl)butanol hydrochloride 13 g of the product obtained above are added dropwise at 0° C. to 9.7 g of Vitride ® in toluene.

The reaction is allowed to proceed for 30 minutes at room temperature, the reaction mixture is then poured into water and extracted with ether and the extract is washed with a saturated aqueous solution of sodium chloride and dried over magnesium sulfate. It is evaporated to dryness and the product is then taken up in a solution of hydrogen chloride in ether. After evaporation, the product is taken up in 20 ml of ethanol and then precipitated in ether. The precipitate is washed with ether and then dried in vacuo to give 8 g of the expected product.

Yield: 61%.

Melting point: 185°–186° C.

(B) SR 44541 A 2.1 g of the product prepared in the previous step and 5 g of 2,4-dichlorophenoxyacetyl chloride are refluxed for 2 hours in 50 ml of dichloroethane. The volume is halved by evaporation in vacuo, the mixture is then precipitated in ether and the precipitate is filtered off, washed with ether and dried in vacuo to give 2.7 g of product, which is recrystallized from ether.

Yield: 90%.

Melting point: 92° C.

EXAMPLES 5 to 42

The products according to the invention which are described in Table I below were prepared by using the same methods as those given above. These products are characterized by their melting points (m.p.) after recrystallization from a solvent. The recrystallization solvents (solvent) are used pure or as mixtures of equal volumes. The abbreviations have the following meanings:

| | |
|---|---|
| Methyl alcohol | MeOH |
| Ethyl alcohol | EtOH |
| Isopropyl alcohol | iPrOH |
| Ethyl ether | Et$_2$O |
| Isopropyl ether | (iPr)$_2$O |
| Dichloromethane | DCM |
| Dichloroethane | DCE |

The products obtained in the form of oils are characterized by their NMR spectra run in DMSO at 250 MHz.

The chemical shifts (delta) are measured in ppm; the following abbreviations are used:

s for singlet
d for doublet
t for triplet
m for multiplet

TABLE I $$\begin{array}{c} R_1 \\ \diagdown \\ N-(CH_2)_n-CH-CH_2-O-\underset{\underset{O}{\|}}{C}-Y-R_5 \cdot HCl \\ \diagup \\ R_2 \end{array}$$

with aryl groups bearing $R_3$, $R_4$ substituents

| Ex. no. | Product SR | NR$_1$R$_2$ | n | R$_4$ | —Y— | R$_5$ | M.p. °C. solvent |
|---|---|---|---|---|---|---|---|
| 5 | 44026 A | hexamethyleneimino | 2 | naphth-2-yl | — | 2,4-Cl phenyl | 179–182 EtOH/Et$_2$O |
| 6 | 44085 A | dimethylamino | 2 | naphth-1-yl | — | phenyl | 133–136 iPrOH/Et$_2$O |
| 7 | 44086 A | 1,2,3,4-tetrahydroisoquinolyl | 2 | naphth-1-yl | — | 2,4-Cl phenyl | 198–200 iPrOH/Et$_2$O |
| 8 | 44099 A | hexamethyleneimino | 2 | 2,4-Cl phenyl | — | 2,4-Cl phenyl | 144–146 MeOH/Et$_2$O |
| 9 | 44100 A | hexamethyleneimino | 2 | 2,4-Cl phenyl | — | 4-Cl phenyl | 181–184 MeOH/Et$_2$O |
| 10 | 44101 A | hexamethyl- | 2 | 2,4-Cl | — | 4-F | 182–183 |

TABLE I-continued $$R_1R_2N-(CH_2)_n-CH-CH_2-O-\underset{\underset{O}{\|}}{C}-Y-R_5 \cdot HCl$$

with aryl group bearing $R_3$, $R_4$ substituents and $R_5$ aryl bearing $R_3$, $R_4$.

| Ex. no. | Product SR | NR₁R₂ | n | R₃ R₄ | —Y— | R₅ | M.p. °C. solvent |
|---|---|---|---|---|---|---|---|
| | | leneimino | | phenyl | | phenyl | iPrOH/Et₂O |
| 11 | 44149 A | piperidino | 2 | naphth-1-yl | — | 4-Cl phenyl | 194–196 iPrOH/Et₂O |
| 12 | 44150 A | piperidino | 2 | naphth-1-yl | — | 3-Cl phenyl | 88–91 iPrOH/Et₂O |
| 13 | 44151 A | piperidino | 2 | naphth-1-yl | — | 2-Cl phenyl | 132–134 (iPr)₂O |
| 14 | 44152 A | piperidino | 2 | naphth-1-yl | — | 2,4-Cl phenyl | 187–190 EtOH/Et₂O |
| 15 | 44194 A | imidazolyl | 2 | naphth-1-yl | — | 2,4-Cl phenyl | 130–134 iPrOH/Et₂O |
| 16 | 44225 A | diisopropylamino | 2 | naphth-1-yl | — | 2,4-Cl phenyl | 169–172 iPrOH/Et₂O |
| 17 | 44384 A | dimethylamino | 2 | naphth-1-yl | CH=CH | 2,4-Cl phenyl | 133–134 DCE/Et₂O |
| 18 | 44385 A | dimethylamino | 2 | naphth-1-yl | — | 3-CF₃ phenyl | 152–154 Et₂O |
| 19 | 44417 A | piperidino | 3 | biphenylyl | — | 2,4-Cl phenyl | 128–130 Et₂O |
| 20 | 44418 A | piperidino | 3 | biphenylyl | — | 2,4-Cl phenyl | 141–143 Et₂O |
| 21 | 44427 A | dimethylamino | 2 | naphth-1-yl | CH₂S | phenyl | 113 Et₂O |
| 22 | 44428 A | dimethylamino | 3 | 3,4-Cl phenyl | — | 2,4-Cl phenyl | 117 EtOH/Et₂O |
| 23 | 44430 A | dimethylamino | 2 | naphth-1-yl | CH=CH | 4-Cl phenyl | 182 EtOH/Et₂O |
| 24 | 44431 A | hexamethyleneimino | 2 | 3,4-Cl phenyl | CH=CH | 2,4-Cl phenyl | 200–202 EtOH/Et₂O |
| 25 | 44433 A | hexamethyleneimino | 2 | 3,4-Cl phenyl | — | cyclohexyl | 210–212 EtOH/Et₂O |
| 26 | 44537 A | morpholino | 2 | 2,4-Cl phenyl | — | biphenylyl | 180 iPrOH |
| 27 | 44538 A | 4-benzylpiperidino | 2 | naphth-1-yl | — | phenyl | 134 Et₂O |
| 28 | 44539 A | morpholino | 2 | 2,4-Cl phenyl | — | 2,4-Cl phenyl | 138 iPrOH/Et₂O |
| 29 | 44540 A | morpholino | 2 | 2,4-Cl phenyl | — | naphth-1-yl | 176 iPrOH |
| 30 | 44603 A | dimethylamino | 3 | naphth-1-yl | — | 2,4-Cl phenyl | 128–130 DCM/Et₂O |
| 31 | 44661 A | dimethylamino | 3 | naphth-1-yl | — | 4-F phenyl | 103–105 iPrOH/Et₂O |
| 32 | 44699 A | dimethylamino | 3 | naphth-1-yl | — | 4-I phenyl | 184–185 iPrOH/Et₂O |
| 33 | 44700 A | dimethylamino | 3 | naphth-1-yl | — | C₁₀H₂₃ | 71–73 EtOH |
| 34 | 44888 A | diethylamino | 3 | 4-Br phenyl | CH=CH | 4-Cl phenyl | 129–130 iPrOH/Et₂O |
| 35 | 44945 A | dimethylamino | 6 | naphth-1-yl | — | 2,4-Cl phenyl | oily (NMR) |
| 36 | 45026 A | diethylamino | 6 | naphth-1-yl | — | 2,4-Cl phenyl | oily (NMR) |
| 37 | 45029 A | dimethylamino | 6 | naphth-1-yl | — | C₁₀H₂₃ | oily (NMR) |
| 38 | 45031 A | dimethylamino | 6 | 4-Br phenyl | — | 2,4-Cl phenyl | 55–58 iPrOH/Et₂O |
| 39 | 45179 A | dimethylamino | 3 | 4-Br phenyl | — | 2,4-Cl phenyl | 116–118 iPrOH/Et₂O |
| 40 | 45262 A | dimethyl- | 3 | naphth- | — | 3,5-NO₂ | 218–220 |

TABLE I-continued $$R_1\text{\textbackslash}N-(CH_2)_n-CH-CH_2-O-\underset{\underset{O}{\parallel}}{C}-Y-R_5 \cdot HCl$$
$$R_2/$$

(with phenyl ring bearing $R_3$, $R_4$; alternative naphthyl with $R_3$, $R_4$)

| Ex. no. | Product SR | $NR_1R_2$ | n | $R_3$ $R_4$ | —Y— | $R_5$ | M.p. °C. solvent |
|---|---|---|---|---|---|---|---|
| 41 | 45349 A | dimethyl-amino | 3 | naphth-1-yl | — | phenyl $(CH_2)_{16}$—$CH_3$ | 66–68 Et$_2$O/EtOH Et$_2$O |
| 42 | 45350 A | dimethyl-amino | 3 | naphth-1-yl | — | $(CH_2)_4$—$CH_3$ | 87–89 Et$_2$O |

NMR SPECTRA

SR 44945 A (Example 35):

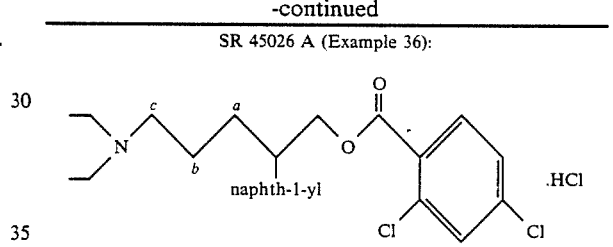

| Delta ppm | Appearance | Protons | Assignment |
|---|---|---|---|
| 1.18 | m | 6H | CH$_2$ a,b,c |
| 1.5 | m | 2H | CH$_2$ d |
| 1.85 | m | 2H | CH$_2$ e |
| 2.59 | s | } 6H | (CH$_3$)$_2$N |
| 2.61 | s | | |
| 2.85 | m | 2H | CH$_2$ f |
| 4 | m | 1H | C$\underline{H}$CH$_2$OCO |
| 4.5 | d J = 7Hz | 2H | CHC$\underline{H}_2$OCO |
| 7.3–8.3 | unresolved signals | 10H | aromatic H |

SR 45026 A (Example 36):

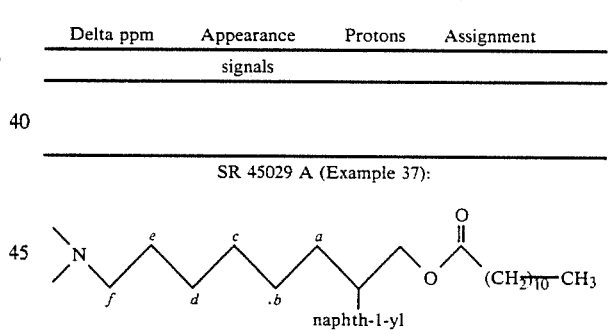

| Delta ppm | Appearance | Protons | Assignment |
|---|---|---|---|
| 1.05 | m | 6H | 2CH$_3$ (ethyl) |
| 1.58 | m | 2H | CH$_2$ a |
| 1.92 | m | 2H | CH$_2$ b |
| 2.92 | m | 6H | 2CH$_2$ (ethyl) + CH$_2$ c |
| 4.05 | m | 1H | C$\underline{H}$CH$_2$OCO |
| 4.5 | d J = 7Hz | 2H | CHC$\underline{H}_2$OCO |
| 7.3–8.3 | unresolved | 10H | aromatic H |

SR 45026 A (Example 36):

| Delta ppm | Appearance | Protons | Assignment |
|---|---|---|---|
| signals | | | |

SR 45029 A (Example 37):

| Delta ppm | Appearance | Protons | Assignment |
|---|---|---|---|
| 0.8 | t J = 6Hz | 3H | C$\underline{H}_3$(CH$_2$)$_{10}$ |
| 0.9–1.5 | unresolved signals | 26H | CH$_2$ a,b,c,d + CH$_2$—(C$\underline{H}_2$)$_9$—CH$_3$ |
| 1.75 | m | 2H | CH$_2$ c |
| 2–2.3 | unresolved signals | 10H | (CH$_3$)$_2$N + CH$_2$CO + CH$_2$ f |
| 3.8 | m | 1H | C$\underline{H}$CH$_2$OCO |
| 4.22 | m | 2H | CHC$\underline{H}_2$OCO |
| 7.3–8.2 | unresolved signals | 7H | aromatic H |

The bactericidal activity of the products according to the invention was studied on different strains by the method described below:

A bacterial inoculum is brought into contact with different dilutions of the test product for a limited period of time: 30 minutes. When the contact period has ended, an aliquot of the mixture of bacterial suspension and product is deposited on the surface of an agar culture medium containing an agent for neutralizing the antibacterial activity of the product. The bactericidal concentration considered is the minimum concentration of product above which the bacteria no longer grow. This concentration is expressed in µg/ml.

The bacterial strains selected for the study are as follows:
1-Escherichia coli CNCM 54125
2-Klebsiella pneumoniae capsulée acid RO30
3-Pseudomonas aeruginosa CNCM A22
4-Streptococcus faecalis CNCM 5855
5-Staphylococcus aureus CNCM 53154

The second strain is maintained on Worgel Fergusson medium and the others on Tryptic Soy Agar-Difco (TSA) marketed by Difco.

After cultivation for 24 hours at 37° C., the microbial growth is harvested with the aid of glass beads and 10 ml of diluent containing 1 g of tryptone and 8.5 g of sodium chloride in 1000 ml of distilled water. The suspension formed is stirred and the percentage transmission of light at 620 nm is measured in a spectrophotometer:

|  |  |
|---|---|
| Strain 1: | 70% |
| Strain 2: | 80% |
| Strain 3: | 70% |
| Strain 4: | 60% |
| Strain 5: | 60% |

The bacterial inoculum corresponds to a 1:20 dilution of this bacterial suspension.

Plates containing cups receive different dilutions of the test product. These dilutions of the test product are brought into contact with the different bacterial suspensions with the aid of a multiple-site inoculator. After a contact period of 20 minutes, aliquots are transferred with the aid of this inoculator to the surface of an agar medium (TSA) placed in Petri dishes and containing an agent for neutralizing the activity, namely 20 g of Lubrol W, 25 g of Tween 80 and 2.5 g of sodium thiosulfate in 1000 ml of TSA (Difco). A reference for the efficacy of the neutralizing agent is prepared for each test product by depositing an aliquot of the dilution of the test product on the surface of the culture medium. After drying, the corresponding inoculum is deposited in the same place. A corresponding reference inoculum is deposited in the same place. A reference inoculum is prepared on agar medium with and without neutralizing agent. The results are read off after incubation for 48 hours at 37° C.

The results obtained with the compounds of the examples, which are identified by both their example number and the internal reference of the Applicant Company (SR), are collated in TABLE II below.

TABLE II

| | | Minimum bactericidal concentration (MBC) in µg/ml | | | | |
|---|---|---|---|---|---|---|
| Ex. no. | Product number | \multicolumn{5}{c}{Bacterial strain} | | | | |
| | | 1 | 2 | 3 | 4 | 5 |
| 5 | SR 44026 A | 10 | 50 | 50 | 10 | 10 |
| 1 | SR 44083 A | 5 | 10 | 50 | 10 | 50 |
| 6 | SR 44085 A | 50 | 50 | 50 | 50 | 100 |
| 7 | SR 44086 A | 50 | 50 | 100 | 50 | 500 |
| 8 | SR 44099 A | 5 | 50 | 50 | 5 | 50 |
| 9 | SR 44100 A | 5 | 50 | 50 | 10 | 100 |
| 10 | SR 44101 A | 5 | 10 | 50 | 10 | 200 |
| 2 | SR 44102 A | 5 | 50 | 50 | 5 | 10 |
| 11 | SR 44149 A | 10 | 10 | 50 | 10 | 50 |
| 12 | SR 44150 A | 10 | 50 | 50 | 50 | 50 |

TABLE II-continued

| | | Minimum bactericidal concentration (MBC) in µg/ml | | | | |
|---|---|---|---|---|---|---|
| Ex. no. | Product number | \multicolumn{5}{c}{Bacterial strain} | | | | |
| | | 1 | 2 | 3 | 4 | 5 |
| 13 | SR 44151 A | 50 | 50 | 100 | 50 | 500 |
| 14 | SR 44152 A | 10 | 10 | 100 | 10 | 50 |
| 15 | SR 44194 A | 50 | 50 | 50 | 50 | 500 |
| 16 | SR 44225 A | <10 | 50 | 100 | <10 | 500 |
| 17 | SR 44384 A | 10 | 10 | 10 | 10 | 10 |
| 18 | SR 44385 A | 10 | 50 | 50 | 10 | 50 |
| 19 | SR 44417 A | 5 | 5 | 50 | 5 | 5 |
| 20 | SR 44418 A | 10 | 10 | 50 | 50 | 50 |
| 21 | SR 44427 A | 50 | 50 | 50 | 50 | 500 |
| 22 | SR 44428 A | 5 | 5 | 10 | 10 | 10 |
| 3 | SR 44429 A | 5 | 5 | 10 | 5 | 5 |
| 23 | SR 44430 A | 5 | 5 | 10 | 5 | 10 |
| 24 | SR 44431 A | 1 | 5 | 5 | 5 | 5 |
| 25 | SR 44433 A | 50 | 50 | 50 | 50 | 500 |
| 26 | SR 44537 A | 50 | — | 100 | 50 | 500 |
| 27 | SR 44538 A | 10 | — | 100 | 50 | 100 |
| 28 | SR 44539 A | 50 | — | 100 | 50 | 500 |
| 29 | SR 44540 A | 50 | — | 100 | 50 | 500 |
| 4 | SR 44541 A | 10 | — | 50 | 50 | 50 |
| 30 | SR 44603 A | 5 | — | 5 | 10 | 10 |
| 31 | SR 44661 A | 50 | — | 50 | 50 | 50 |
| 32 | SR 44699 A | 5 | — | 50 | 5 | 200 |
| 33 | SR 44700 A | 2 | — | 5 | 2 | 2 |
| 34 | SR 44888 A | 10 | — | 10 | 10 | 10 |
| 35 | SR 44945 A | 5 | — | 5 | 5 | 5 |
| 36 | SR 45026 A | 10 | — | 50 | 10 | 200 |
| 37 | SR 45029 A | 10 | — | 10 | 5 | 10 |
| 38 | SR 45031 A | 5 | — | 10 | 5 | 10 |
| 39 | SR 45179 A | 10 | — | 50 | 50 | 50 |
| 40 | SR 45262 A | 50 | — | 200 | 50 | 50 |

The results show that the products according to the invention have a broad spectrum of activity against the bacterial strains tested. This bactericidal activity is expressed within a short period of time (less than or equal to 30 minutes).

The antifungal activity of the products according to the invention was also determined using the method described above.

A representative strain of yeasts, Candida albicans CNCM 1180, was selected for the study.

It is maintained on a medium of Sabouraud Dextrose Agar marketed by Difco and the technique is identical to that described for the study of the anti-bacterial activity. After cultivation for 48 hours at 37° C., the microbial growth is harvested with the aid of glass beads and 5 ml of diluent containing 1 g of tryptone and 8.5 g of sodium chloride in 1000 ml of distilled water; a further 5 ml of the diluent are then added. In the spectrometer, this suspension gives a 2 to 3% transmission of light at 620 nm. A 1:100 dilution of this suspension, observed between a slide and a cover glass with the 40 lens of a microscope, must show 10 cells per field, which corresponds to 1,000,000 yeasts per ml.

The results obtained with compounds according to the examples are collated in TABLE III below.

TABLE III

| | Minimum fungicidal concentration (MFC) in µg/ml | |
|---|---|---|
| Ex. no. | Product | MFC |
| 5 | SR 44026 A | 50 |
| 1 | SR 44083 A | 10 |
| 6 | SR 44085 A | 100 |
| 7 | SR 44099 A | 50 |
| 2 | SR 44102 A | 50 |
| 11 | SR 44149 A | 100 |
| 12 | SR 44150 A | 100 |
| 17 | SR 44384 A | 50 |
| 24 | SR 44431 A | 10 |

TABLE III-continued

Minimum fungicidal concentration (MFC) in μg/ml

| Ex. no. | Product | MFC |
|---|---|---|
| 26 | SR 44537 A | 100 |
| 27 | SR 44538 A | 100 |
| 28 | SR 44539 A | 100 |
| 29 | SR 44540 A | 100 |
| 4 | SR 44541 A | 50 |
| 30 | SR 44603 A | 10 |
| 31 | SR 44661 A | 200 |
| 32 | SR 44699 A | 50 |
| 33 | SR 44700 A | 2 |
| 34 | SR 44888 A | 50 |
| 35 | SR 44945 A | 5 |
| 37 | SR 45029 A | 10 |
| 38 | SR 45031 A | 10 |
| 39 | SR 45179 A | 50 |
| 40 | SR 45262 A | 200 |

These results show that the products according to the invention possess a valuable antifungal activity which takes effect quickly.

The tolerance of the products according to the invention was studied on guinea-pigs. The animals are shaved on either side of the median line of the back and this is repeated every 2 days. Groups of 6 animals receive 0.2 ml of an aqueous or alcoholic solution of the product according to the invention on the shaved area. If the products are in alcoholic solution, a control group of animals receives the alcohol on one side.

For studying the skin tolerance, the treatment is applied once a day for 6 out of 7 days over a period of 3 weeks. The observations relating to the skin involve the presence of erythema, skin eruption or hyperkeratosis, the intensity of which is graded according to a given scale.

The skin sensitization test is performed on the same animals after a break of two weeks. The treatment lasts for one week and is identical to the previous treatment. The results are evaluated according to the same criteria and on the same scale as that used for the local tolerance.

The products according to the invention were found to be tolerated well when applied in concentrations ranging up to 2%. Furthermore, they have no sensitizing effect.

The acute toxicity by oral administration was evaluated on mice. This study was carried out on male mice of the CD1 strain, originating from the Charles River breeding station. Each group was made up of 5 animals with a body weight varying from 24 to 30 g, which were kept in the same cage. The animals were fasted for 6 hours before the treatment. For each study, a suspension of the product in a 10% solution of gum arabic was administered by gavage with the aid of an esophageal tube. The animals were given food again 4 hours after gavage and kept under observation for a period of 14 days after administration. During this period, the mortality is noted in each of the groups taking part in the experiment and, where possible, the 50% lethal dose ($LD_{50}$) is determined using the method of J. T. LITCHFIELD and R. WILCOXON, J. Pharmacol. 1949, 95, 99-113. The oral $LD_{50}$ of the products according to the invention was found to be greater than 1000 mg/kg.

The products according to the invention, which have a good antimicrobial activity, can be used in pharmaceutical, disinfectant, cosmetic or food preparations, especially as antiseptics by local and general application, as disinfectants and as preservatives.

As antiseptics for human or veterinary use, the concentration of active product can vary from 0.01% to 5% according to the use and the chosen formulation. Thus, it is possible to prepare foaming detergent solutions to be used by surgeons and nursing staff for washing their hands or to be used for cleansing dermatological lesions such as impetigo, pityriasis and leg ulcers. Foaming detergent solutions are also used as shampoos (for example antidandruff shampoos) or for the preparation of shower gels, shaving creams and foaming lotions. Foaming solutions containing products according to the invention are obtained using amphoteric, anionic, cationic or non-ionic surfactants at a concentration of 0.3 to 30%, humectants, such as glycols or polyethylene glycols, at a concentration of 0 to 20%, ethylene oxide and polypropylene copolymers at a concentration of 0 to 20%, and an alcohol (ethanol, isopropanol, benzyl alcohol) or a polyol, such as glycerol, at a concentration of 0 to 15%, as well as agents for complexing $Ca^{++}$, $Mg^{++}$ and heavy metal ions, salts for providing an appropriate buffer capacity, agents for imparting viscosity, such as NaCl or KCl, natural, cellulosic or synthetic polymers such as polyvinylpyrrolidone, thickening superfatting agents such as polyethylene glycol distearate or copra monoethanolamide or diethanolamide, fragrances, preservatives and colorants.

If the product according to the invention has a poor solubility in water, it is possible to use microemulsions, micellar solutions or any other phase of the ternary or quaternary diagram of water/active principle/surfactant/co-surfactant which permits solubilization in water. These solutions can be used in diluted or undiluted form and can be dispensed for example by means of a vasopump or liquefied or non-liquefied propellants.

With the same constituents at appropriate concentrations, the products according to the invention can also be used to prepare simple aqueous solutions or aqueous solutions in the form of sprays for making operative fields antiseptic, for postoperative treatments, for the treatment of burns, superinfected eczema, gluteal erythema, wounds or acne, or for deodorants.

Simple alcoholic solutions or alcoholic solutions in the form of sprays containing 20 to 80% of alcohol can contain, apart from the excipients used in aqueous solutions, excipients which make it possible to penetrate the keratinized layers of the skin and superficial body growths, such as Azone (marketed by Nelson Research) and Transcutol (marketed by Gattefossé). These solutions are to be used for making the skin antiseptic before puncture, for preparing the operative field, by nursing staff for making their hands antiseptic and for treating closed infected dermatosis, folliculitis, perionychia or acne.

The products according to the invention can be applied in the form of creams which contain some of the compounds mentioned for the preparation of solutions, together with the fatty substances normally found in the preparation of creams or emulsions. These creams can be used especially for the prevention of superinfections of gluteal erythema, eczema, mycosis or acne.

The products according to the invention can also be used for the treatment or prevention of sexually transmitted diseases, in the form of pessaries, gynecological tablets or gynecological sponges or as a complement for contraceptives. The pessaries can contain from 0 to 99% of triglycerides, polyethylene glycols of different molecular weights, Tweens, natural or synthetic polymers, polyols and soaps. The gynecological tablets can contain diluents such as lactose or cellulose, lubricants such as magnesium stearate, flow enhancers such as silica, and disintegrating agents such as carboxymethyl starch or cellulose.

The products according to the invention can be administered in the form of sprays, with nose and mouth nozzles, for treating infectious syndromes of the respiratory tract (rhinitis, sinusitis, sore throat, amygdalitis, pharyngitis), or in the form of gels or mouthwashes for treating gingivitis or pyorrhea or preventing dental plaque, in which case it is also possible to use toothpastes containing the products according to the invention. The forms for oral or nasal administration can contain the same excipients as the solutions, to which flavorings are added, if appropriate, in the case of the oral forms or the constituents necessary for isotonicity are added, if appropriate, in the case of the nasal sprays; the toothpastes also contain pyrogenic or non-pyrogenic colloidal silicas, calcium carbonate, sweeteners and fluorine salts.

The products according to the invention can be used in eye lotions, eye solutions or ophthalmic ointments for treating eye infections (for example blepharitis or conjunctivitis), or in liquids for rinsing contact lenses. These forms for the eyes can be prepared using the same constituents as those used for the solutions, care being taken to ensure that the mixture is isotonic.

Furthermore, the products according to the invention can be administered to man by a general route, for example orally, in the form of gelatin capsules, ordinary tablets or enteric tablets, as intestinal antiseptics.

The products according to the invention can also be used in animals for indications such as the prevention or treatment of infected lesions or lesions liable to become superinfected. In this case, the pharmaceutical compositions are similar to those used in man, in particular creams, sprays or solutions.

Moreover, the rapid lethal action on germs of the products according to the invention enables them to be used as surface disinfectants at concentrations which can vary from 0.1 to 4%. In this case, the products are used in preparations such as aqueous or non-aqueous foaming detergent solutions, sprays or nebulizers. Preparations of this type are particularly useful in the hospital or veterinary sectors, for local communities or agrifoodstuff industries. These preparations can contain the same constituents as those used in the antiseptic formulations, although a variety of organic solvents may be added.

Finally, the antimicrobial activity of these products enables them to be used as preservatives in the pharmaceutical, cosmetic and food industries. In this case, the products according to the invention are used as additives for pharmaceutical, cosmetic or food formulations at concentrations which can vary from 0.005 to 0.5%. These compounds can also be used as disinfectant additives in paints.

Different formulations of the products according to the invention can be prepared according to the chosen application.

EXAMPLE 43

Foaming antiseptic liquid detergent preparation

| | |
|---|---|
| SR 44102 A | 0.5 g |
| Sodium paraffinsulfonate | 15 g |
| Sodium hydroxide or lactic acid qs pH 5.2 | |
| Purified water qs | 100 g |

EXAMPLE 44

Alcoholic antiseptic solution

| | |
|---|---|
| SR 44384 A | 0.2 g |
| Alkyldimethylcarboxymethylamine (30% solution) | 0.5 g |
| Condensation product of ethylene oxide and propylene glycol L 62 | 1 g |
| Lactic acid or sodium hydroxide qs pH 6.5 | |
| 70° ethyl alcohol qs | 100 g |

EXAMPLE 45

Foaming antiseptic liquid detergent preparation

| | |
|---|---|
| SR 44083 A | 0.1 g |
| Alkyldimethylcarboxymethylamine (30% solution) | 15 g |
| Disodium tetracemate | 0.1 g |
| Propylene glycol | 20 g |
| Sodium hydroxide qs pH 5.8 | |
| Purified water qs | 100 g |

EXAMPLE 46

Mouthwash

| | |
|---|---|
| SR 44083 A | 0.3 g |
| 95° ethyl alcohol | 14 g |
| Essence of aniseed | 0.00225 ml |
| Eugenol | 0.00075 ml |
| Glycerol | 20 ml |
| Saccharin | 0.03 g |
| Sodium hydroxide solution qs pH 5.5 | |
| Purified water qs | 100 ml |

EXAMPLE 47

Antiseptic pessaries for treating sexually transmitted diseases

| | |
|---|---|
| SR 44431 A | 500 mg |
| Eutectic mixture of fatty acid esters | 2.568 g |

Suppocire A ®, marketed by Gattefossé, can be used as the eutectic mixture of fatty acid esters.

EXAMPLE 48

Eye lotion

| | |
|---|---|
| SR 44603 A | 0.2 g |
| Sodium chloride | 1.4 g |
| Water for injectable preparations qs | 100 ml |

EXAMPLE 49

Enteric tablets

| | |
|---|---|
| SR 44384 A | 200 mg |
| Hydroxypropylmethyl cellulose 6 cP | 6 mg |
| Lactose | 114 mg |
| Microcrystalline cellulose | 60 mg |
| Sodium carboxymethyl starch | 12 mg |
| Magnesium stearate | 8 mg |
| For one finished uncoated tablet of 400 mg | |

Coating

| | |
|---|---|
| Eudragit L 100 | 0.9 mg |
| Dibutyl phthalate | 0.9 mg |
| Acetone | 14.1 mg |
| Isopropyl alcohol | 14.1 mg |
| For one finished coated tablet of 430 mg | |

EXAMPLE 50

Spray

| | |
|---|---|
| SR 44026 A | 2 g |
| 95° ethanol | 20 g |
| Propylene glycol | 5 g |
| Na hydroxide qs pH 5.5 | |
| Water qs | 100 g |
| Propellant qs | |

EXAMPLE 51

Film-forming spray

| | |
|---|---|
| SR 44083 A | 0.5 g |
| Polyvinylpyrrolidone | 2 g |
| Acrylic resin | 2 g |
| 95° ethanol qs | 100 g |
| propellant qs | |

EXAMPLE 52

A product according to the invention can be used as a preservative in a cream emulsion

| | |
|---|---|
| Liquid paraffin | 6 g |
| Mixture of cetostearyl alcohol and ethoxylated cetostearyl alcohol | 9 g |
| Anhydrous monosodium phosphate | 0.300 g |
| Disodium tetracemate | 0.010 g |
| Petroleum jelly | 15 g |
| SR 44429 A | 0.100 g |
| Phosphoric acid qs pH 4.5 | |
| Purified water qs | 100 g |

EXAMPLE 53

A product according to the invention can be used as a preservative in a cream for cosmetological use.

| | |
|---|---|
| Collagen | 0.500 g |
| Carboxypolymethylene 934 | 0.400 g |
| Hydrogenated lanolin | 4 g |
| Perhydrosqualene | 20 g |

-continued

| | |
|---|---|
| Polyethoxylated sorbitol monopalmitate | 2 g |
| SR 44428 A | 0.150 g |
| Lactic acid or sodium hydroxide qs pH 6.5 | |
| Purified water qs | 100 g |

EXAMPLE 54

Preservative in a suntan oil

| | |
|---|---|
| Mineral oil 65/75 | 68 g |
| Castor oil | 8 g |
| Sesame oil | 20 g |
| Isopropyl alcohol | 2 g |
| Eusolex ® | 1.5 g |
| Fragrance | 0.4 g |
| SR 44430 A | 0.100 g |

EXAMPLE 55

A product according to the invention can be used as a preservative in a shampoo.

| | |
|---|---|
| Potassium amino acid palmitate | 20 g |
| Sodium alkyl-sulfates | 2 g |
| Copra diethanolamide | 5 g |
| Linalyl acetate | 0.200 g |
| SR 44431 A | 0.05 g |
| Sodium hydroxide qs pH 7 | |
| Purified water qs | 100 g |

EXAMPLE 56

Preservative for fruit juice or jam

| | |
|---|---|
| Micronized SR 44417 A | 0.02% |

EXAMPLE 57

Disinfectant for inert surfaces

| | |
|---|---|
| SR 44026 A | 2 g |
| Dodecyldimethylcarboxydimethylamine | 20 g |
| Disodium tetracemate | 2 g |
| Lactic acid qs pH 3.5 | |
| Purified water qs | 100 g |

What is claimed is:

1. A compound of the formula:

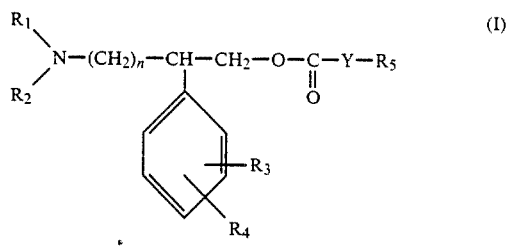

in which:

n is an integer between 2 and 10;

$R_1$ and $R_2$ are identical or different and represent a cycloalkyl containing 3 to 6 carbon atoms or an alkyl containing from 1 to 6 carbon atoms which is unsubstituted or substituted by a phenyl or benzyl group;

$R_3$ represents a hydrogen, a halogen, a methyl or a phenyl;

$R_4$ represents a hydrogen, a halogen or a methyl; or $R_3$ and $R_4$, taken together with the benzene ring to which they are bonded, form a naphth-1-yl or naphth-2-yl group;

Y represents a direct bond, a methyleneoxy group, a methylenethio group or a vinylene group; and $R_5$ represents an alkyl containing from 5 to 18 carbon atoms, a cycloalkyl containing from 3 to 8 carbon atoms, an adamantyl, naphth-1-yl or naphth-2-yl group, an unsubstituted phenyl group or a phenyl group substituted by one or 2 substituents selected from halogen atoms, the trifluoromethyl group, the nitro group and the phenyl group;

and its salts with mineral or organic acids.

2. A compound as claimed in claim 1, wherein $R_3$ represents a hydrogen, a halogen, a methyl or a phenyl and $R_4$ represents a hydrogen, a halogen or a methyl.

3. A compound as claimed in claim 1, wherein $R_3$ and $R_4$, taken together with the benzene ring to which they are bonded, form a naphth-1-yl or naphth-2-yl group.

4. A compound as claimed in claim 3, wherein $R_3$ and $R_4$, taken together with the benzene ring to which they are bonded, form a naphth-1-yl group; n is 2, 3 or 4; and $R_5$ is a phenyl group substituted with one or two halogen atoms.

5. A compound as claimed in claim 1, wherein $R_1$ and $R_2$ are identical or different and represent a cycloalkyl containing 3 to 6 atoms or an alkyl containing from 1 to 6 carbon atoms which is unsubstituted or substituted by a phenyl or benzyl group, and wherein Y is a single bond.

6. 5-Dimethylamino-2-(naphth-1-yl)pentyl 2,4-dichloro-benzoate and its salts.

7. In a pharmaceutical, disinfectant, cosmetic or food composition which contains an effective antimicrobial, disinfectant or preservative amount of an antimicrobial compound as an active ingredient, the improvement wherein said antimicrobial compound is the compound having formula I as claimed in claim 1.

8. A pharmaceutical composition having antimicrobial and disinfectant activity as claimed in claim 7, wherein said effective amount of said antimicrobial compound is from 0.01 to 5% of said compound having formula I.

9. A disinfectant composition for inert surfaces as claimed in claim 7, wherein said effective amount of said antimicrobial compound is from 0.1 to 4% of said compound having formula I.

10. A pharmaceutical composition as claimed in claim 7, wherein said effective amount of said antimicrobial compound as a preservative is from 0.005 to 0.5% of said compound having formula I.

11. A cosmetic product as claimed in claim 7, wherein said effective amount of said antimicrobial compound as a preservative is from 0.005 to 0.5% of said compound having formula I.

12. A foodstuff as claimed in claim 7, wherein said effective amount of said antimicrobial compound as a preservative is from 0.005 to 0.5% of said compound having formula I.

* * * * *